(12) United States Patent
Kim

(10) Patent No.: US 7,506,981 B2
(45) Date of Patent: Mar. 24, 2009

(54) IMAGE ACQUISITION/OUTPUT APPARATUS AND OPHTHALMOLOGY PICTURE SYSTEM USING THE SAME

(76) Inventor: Bong-Hyun Kim, 407-4, Haeri Haenameup, Haenamkoon, Cheonnam, 536-809 (KR)

( * ) Notice: Subject to any disclaimer, the term of this patent is extended or adjusted under 35 U.S.C. 154(b) by 58 days.

(21) Appl. No.: 10/567,123
(22) PCT Filed: Feb. 28, 2005
(86) PCT No.: PCT/KR2005/000542

§ 371 (c)(1),
(2), (4) Date: Nov. 14, 2006

(87) PCT Pub. No.: WO2005/104929

PCT Pub. Date: Nov. 10, 2005

(65) Prior Publication Data

US 2007/0070294 A1    Mar. 29, 2007

(30) Foreign Application Priority Data

Apr. 30, 2004    (KR) .................... 10-2004-0030554

(51) Int. Cl.
*A61B 3/14*    (2006.01)
*A61B 3/10*    (2006.01)
(52) U.S. Cl. ..................... 351/206; 351/221
(58) Field of Classification Search ......... 351/205–206, 351/210, 213, 221
See application file for complete search history.

(56) References Cited

U.S. PATENT DOCUMENTS

| 4,807,989 A | 2/1989 | Nagano et al. ............... 351/212 |
| 5,865,829 A | 2/1999 | Kitajima ........................ 606/3 |
| 5,886,767 A | 3/1999 | Snook ........................ 351/212 |
| 6,089,716 A * | 7/2000 | Lashkari et al. ............. 351/221 |
| 6,525,878 B1 | 2/2003 | Takahashi ................... 359/466 |
| 7,338,168 B2 * | 3/2008 | Cartlidge et al. ............ 351/206 |

FOREIGN PATENT DOCUMENTS

KR    2004-22870 A    3/2004

OTHER PUBLICATIONS

International Search Report for International Application No. PCT/KR2005/000542, mailed on Jul. 11, 2005.

* cited by examiner

*Primary Examiner*—Scott J Sugarman
*Assistant Examiner*—Dawayne A Pinkney
(74) *Attorney, Agent, or Firm*—Harrity & Harrity, LLP

(57) ABSTRACT

The present invention is related to an image acquisition/output apparatus and a picture system for ophthalmic operation using the same. The picture system for ophthalmic operation according to the present invention includes a near-infrared microscope for irradiating an affect part through an objective lens with near-infrared ray emitted from a light source, and transmitting near-infrared images formed by the objective lens to a first and a second ocular lenses, an image acquisition apparatus for converting near-infrared images transmitted to the first and the second ocular lenses into a first and a second electrical image signals for output, and a display apparatus for receiving the first and the second image signals and outputting them in three-dimensional images.

19 Claims, 13 Drawing Sheets

IMAGE ACQUISITION/OUTPUT APPARATUS AND OPHTHALMOLOGY PICTURE SYSTEM USING THE SAME

TECHNICAL FIELD OF THE INVENTION

The present invention relates to a microscope system, more particularly, to an image acquisition/output apparatus for acquiring an image using near-infrared ray and outputting the acquired image, and a microscope system for ophthalmic operation which displays the acquired near-infrared image in 3-dimensions.

BACKGROUND OF THE INVENTION

In general, ophthalmic operations mean eyesight correction surgeries such as lasik, lasek, wavefront and excimer laser, and eye disease treatments such as operations on cataract and glaucoma.

For such ophthalmic operation, high precision and accuracy are required, since it is an important operation to treat human eyes and the size of an affected part is relatively small.

Accordingly, during this ophthalmic operation, there should be provided a picture system for ophthalmic operation to keep observation closely on the affected part and the progress made by the operation, and a microscope for ophthalmic operation is widely used among such microscope systems for ophthalmic operation.

FIG. 1 shows a microscope for ophthalmic operation according to the prior art.

As shown in FIG. 1, the microscope for ophthalmic operation comprises a light source 2, an optical cable 3 for guiding visible light that is emitted from the light source 2 and irradiating it to an affected part 20, an objective lens 4 for magnifying the affected part 20, and an ocular lens 5 for seeing the affected part 20 that is magnified by the objective lens 4 with the naked eye.

Visible light that is emitted from light source 2 is guided by optical cable 3 to be irradiated to the affected part 20, and the operator performs operation while observing the affected part 20 that is magnified by objective lens 4 through ocular lens 5.

However, there are several problems in this type of conventional microscope for ophthalmic operation as described in the following.

First, conventional microscope for ophthalmic operation uses visible light that is emitted from halogen light source as the illumination means to illuminate the affected part 20, but it has a problem in that the visible light may cause damage to the eye system, namely, the affected part 20, and long recovery time is required even when the operation has been finished.

In other words, in case where such visible light is used while performing ophthalmic operation, it may cause damage to the eyeball system, particularly to the retina. Thus, medical reports reveal that the incidence of retinal damages due to visible light from the microscope during operation actually occupies approximately 7~28% of ophthalmic operations that have been conducted until now.

Furthermore, visible light being exposed brightly during operation may cause the patient to lose the sight for some time even when the operation has been finished, and therefore long recovery time is required. This could be compared to the case when a person feels it difficult to see if one looks at the upper beam from a vehicle for a long time and then sees another object.

Second, there is a problem in conventional microscope for ophthalmic operation that an operation is inconvenient and the progress made cannot be examined simultaneously by a plurality of surgeons, since an image of affected part 20 being obtained during the operation should be directly examined by the operator through ocular lens 5.

Moreover, even if an image of affected part 20 is displayed with a monitor, the image of the affected part 20 is merely displayed in two dimensions, thus lacking the real picture, and also there is a problem that it may cause difficulties in the operation for an operator lacking practical experience in ophthalmic operations with such a monitor.

SUMMARY OF THE INVENTION

An object of the invention is to provide a picture system for ophthalmic operation for preventing damage to the eye system caused by visible light.

Another object of the invention is to provide a picture system for ophthalmic operation for displaying an image of affected part in three dimensions.

Still another object of the invention is to provide a picture system for ophthalmic operation for allowing monitoring by a plurality of operators.

Still further object of the invention is to provide a near-infrared image acquisition/output apparatus for acquiring and outputting near-infrared images having simpler structure, and a picture system for ophthalmic operation using the same.

In order to achieve the above-mentioned objects, a picture system for ophthalmic operation according to one embodiment of the present invention comprises a near-infrared microscope for irradiating near-infrared ray emitted from a light source to an affected part through an objective lens, and transmitting near-infrared images formed by the objective lens to a first and a second ocular lenses; an image acquisition apparatus for converting near-infrared images transmitted to the first and the second ocular lenses into a first and a second electrical image signals for output; and a display apparatus for receiving the first and the second image signals, and outputting them in three-dimensional images.

An image acquisition/output apparatus according to one embodiment of the present invention includes a main body and a supporting member for supporting the main body, and the main body comprises an objective lens arranged opposite to an affected part; a beam irradiation unit for irradiating beam having a predetermined wavelength bandwidth to the affected part; and an image acquisition unit for converting the images formed by the objective lens into electrical image signals and outputting them, wherein the beam irradiation unit includes at least two filters having different light sources and transmission bandwidths.

A picture system for ophthalmic operation according to another embodiment of the present invention includes an image acquisition/output apparatus; and a display apparatus for outputting three-dimensional images using the image signals outputted from the image acquisition/output apparatus.

A picture system for ophthalmic operation according to still another aspect of the present invention includes a near-infrared microscope for irradiating near-infrared ray to an affected part by guiding it to an objective lens, and transmitting near-infrared images formed by the objective lens to a left and a right ocular lenses; a beam splitter arranged between the objective lens and the left and the right ocular lenses for dividing the left and the right near-infrared images respectively to transmit them to one side and the other side; a first adaptor connected to one end of the beam splitter for receiving and outputting the left side near-infrared images; a second adaptor connected to the other end of the beam splitter for receiving and outputting the right side near-infrared images;

a first image acquisition apparatus for outputting the left side near-infrared images output from the first adaptor as electrical left side image signals; a second image acquisition apparatus for outputting the right side near-infrared images output from the second adaptor as electrical right side image signals; and a plurality of display apparatuses for receiving the left and the right image signals and outputting them in three-dimensional images respectively.

According to the invention, wherein an affected part, i.e., an eye of the patient, is irradiated by near-infrared ray instead of visible light during operation, it is possible to reduce side effects, such as tissue damages caused when the affected part is irradiated by visible light, or slow recovery time after operation, thereby securing the safety of the operation.

Furthermore, the sense for the real of a display screen can be enhanced when an image of affected part obtained by the left and right side near-infrared sensors is displayed using a HMD or a three-dimensional monitor, and therefore it has an advantage that the operator can conduct a delicate and precise operation.

Moreover, an image of affected part can be obtained by simple operation of inserting the left side ocular lens and the right side ocular lens in near-infrared microscope into the left side ocular lens insertion groove and the right side ocular lens insertion groove according to a first embodiment of the present invention, and also various filters can be selected and where the user prefers it is possible to observe directly through ocular lenses, by dismantling the image acquisition apparatus from near-infrared microscope.

In addition, a system can be realized using an image acquisition/output apparatus according to a second embodiment of the present invention without near-infrared microscope, thereby allowing more inexpensive and economical system configuration.

DETAILED DESCRIPTION OF THE INVENTION

Hereinafter, embodiments of the invention will be described in detail with reference to the accompanying drawings. In order to describe the present invention more clearly, the parts which are not related to the description will be omitted from the drawings, and the same symbols will be given to the similar parts throughout the specification.

Figure 1:
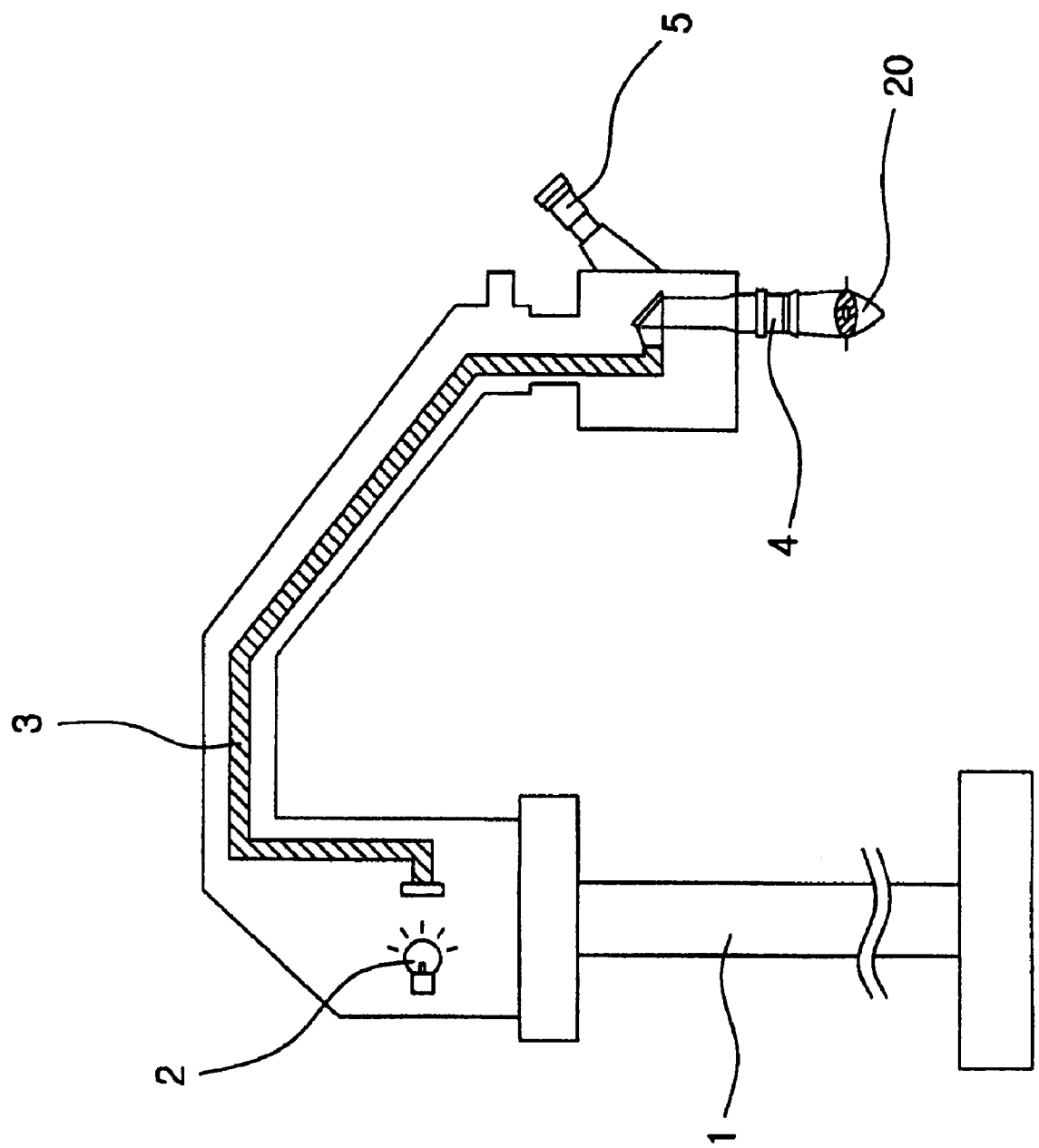
FIG. 1 shows a conventional microscope for ophthalmic operation.
Figure 2:
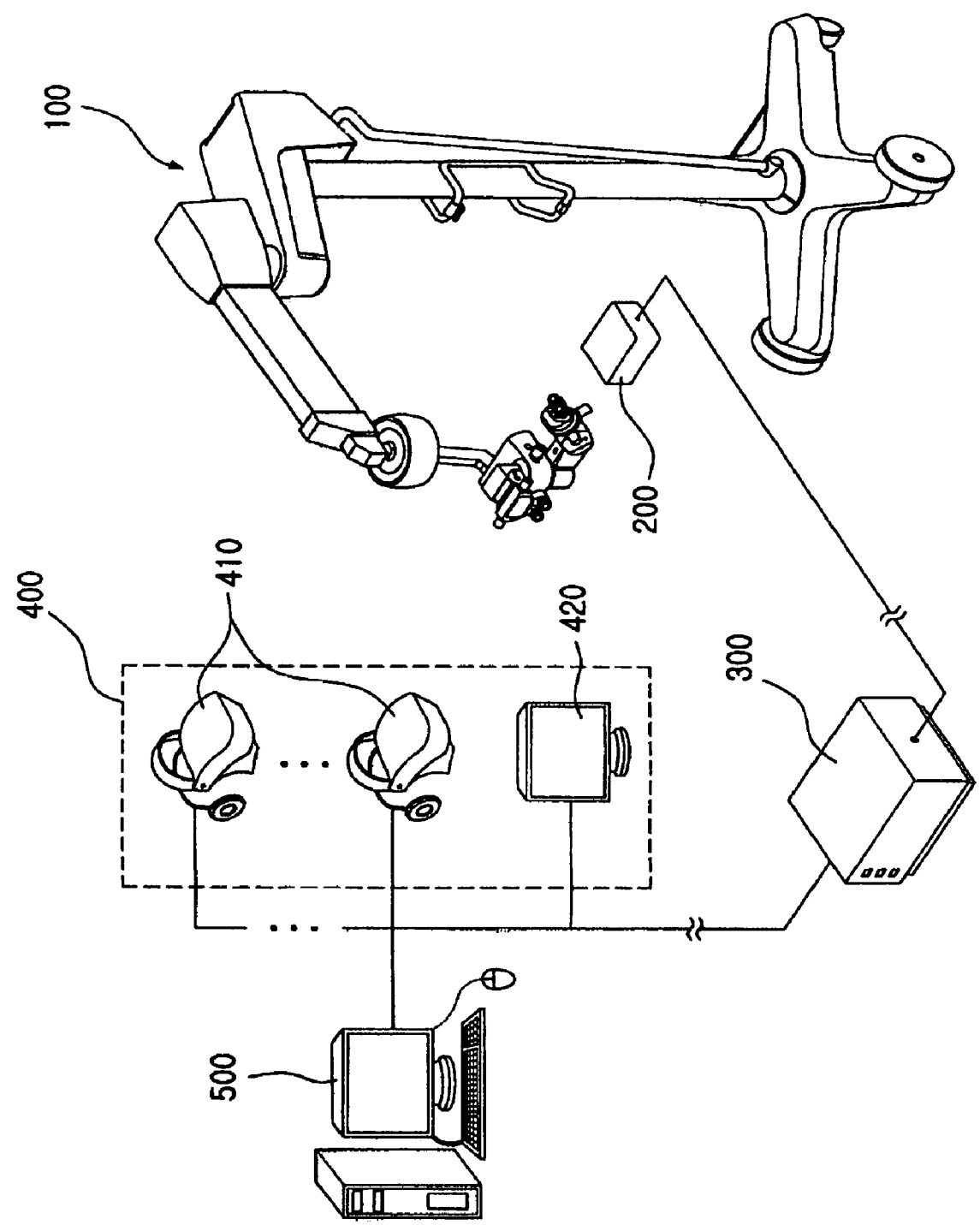
FIG. 2 shows a picture system for ophthalmic operation according to a first embodiment of the present invention.

FIG. 2 is a view showing a picture system for ophthalmic operation according to a first embodiment of the present invention.

As shown in FIG. 2, the picture system for ophthalmic operation according to the first embodiment of the present invention includes a near-infrared microscope 100, an image acquisition apparatus 200, an image distributor 300, a display apparatus 400, and a control/storage apparatus 500. According to the present invention, The microscope 100 irradiates near-infrared ray to an affected part and the image acquisition apparatus 200 acquires a three-dimensional image of affected part.

Here, near-infrared ray has the wavelength within the range of 750~3000 nm, which is invisible by human eyes, and there is an advantage having hardly any side effects such as dazzling of the eyes or slow recovery time after operation, as compared with visible light having the same radiation energy.

Figure 3:
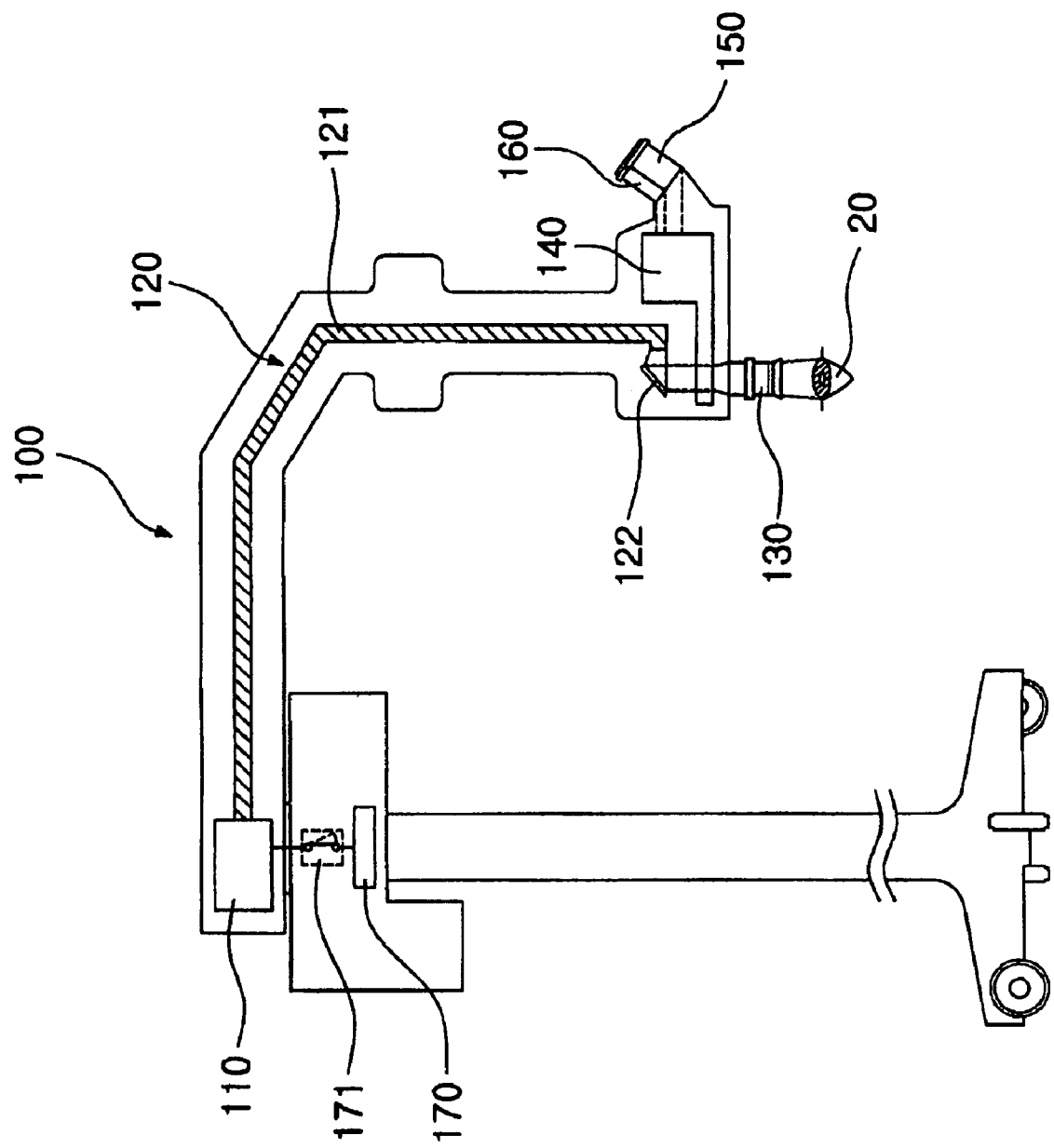
FIG. 3 shows an interior configuration of a near-infrared microscope as shown in FIG. 2.

FIG. 3 is a configuration view schematically showing the near-infrared microscope 100 of FIG. 2.

As shown in FIG. 3, the near-infrared microscope 100 includes a power source 170, a beam generation unit 110, a beam guide unit 120, an objective lens 130, an image transmission unit 140, and ocular lenses 150 and 160.

The near-infrared microscope 100 produces a beam from the beam generation unit 110, and irradiates it to an affected part 20 adjacent to the objective lens 130 by guiding the beam through the beam guide unit 120. Furthermore, it transmits near-infrared images reflected by the affected part 20 to a left side ocular lens 150 and a right side ocular lens 160.

Hereinafter, near-infrared microscope 100 will be described in detail.

First, the beam generation unit 110 produces a beam using the power received from a power source 170, and transmits the beam having near-infrared wavelength bandwidth only to the beam guide unit 120 by filtering the produced beam.

Figure 4:
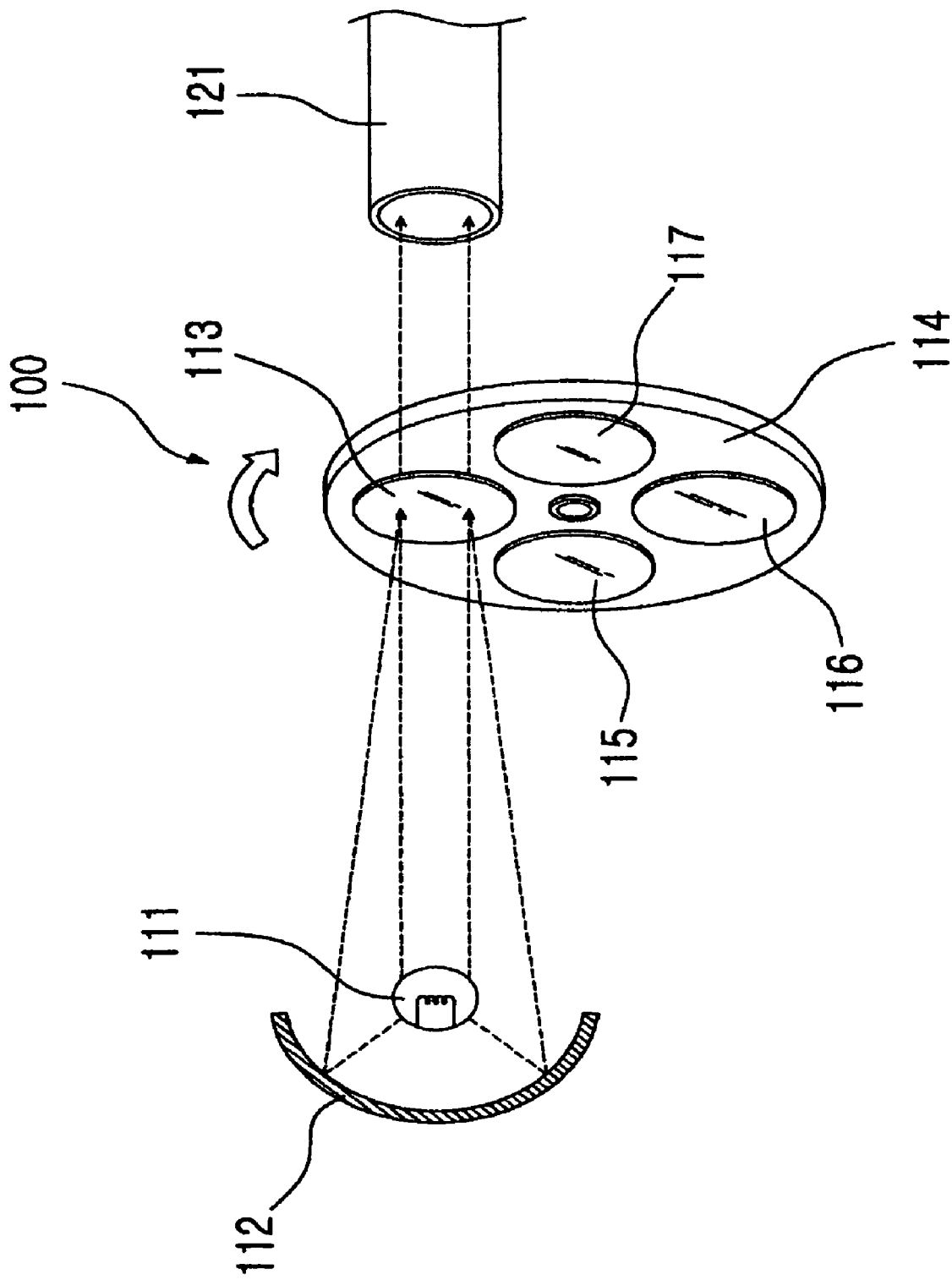
FIG. 4 shows a light source illumination unit shown in FIG. 3 more specifically.

FIG. 4 shows a beam generation unit 110 according to one embodiment of the present invention.

As shown in FIG. 4, the beam generation unit 110 includes a light source 111 for producing a beam by receiving the power, a condensing plate 112 for concentrating the beam generated from the light source 111 into a near-infrared filter 113, and the near-infrared filter 113 for performing a filtering process by reflecting visible light from the received beam and transmitting only near-infrared ray.

Here, when near-infrared filter 113 is formed directly in front of light source 111, a problem causing damage to the near-infrared filter 113 may be produced, since the near-infrared filter 113 absorbs all the radiant energy other than near-infrared ray, and the absorbed energy is saturated thereby. According to one embodiment of the present invention, therefore, the effects of radiant energy impact on the near-infrared filter 113 can be reduced by jointing a visible light reflection filter (not shown) on the front surface of the near-infrared filter 113 using an UV jointing process to reflect visible light by the visible light reflection filter.

The near-infrared filter 113 may be provided in a plate-shaped filter selection unit 114, or multiple filters for passing different wavelengths such as a visible light filter 115, a medium-infrared filter 116 and a far-infrared filter 117 may be provided in the filter selection unit 114 according to the embodiment In this case, user can select the beam having a desired wavelength to irradiate the affected part.

For example, when the user observes an image of affected part 20 through ocular lenses 150, 160 by irradiating visible light to the affected part 20, it is possible to exclude other beams and irradiate visible light only to the affected part by selecting the visible light pass filter 115 from among the filters 113, 115~117 provided in the filter selection unit 114. Using this, the user can observe the affected part through ocular lenses 150, 160 after dismantling the image acquisition apparatus 200.

Furthermore, according to one embodiment of the present invention, damage caused by thermal expansion may be prevented and also proper resilience may be maintained by mounting each filter on the filter selection unit 114 using Teflon tape.

Moreover, though the beam generation unit 110 as disclosed above can produce near-infrared ray using a light source 111 and a near-infrared filter 113, the beam generation unit 110 can also be realized by replacing the light source 111 itself with a near-infrared generation source, such as near-infrared LED (not shown) without having such a near-infrared filter 113.

Furthermore, a switch 171 for turning the power on or off may be provided between a power source 170 and a beam generation unit 110, and therefore it is possible to observe an affected part 20 using natural light without light source, since the beam is not produced by blocking the power supplied to the beam generation unit 110, when the switch 171 is turned off.

Moreover, near-infrared ray produced by this beam generation unit 110 is guided to an objective lens 130 to irradiate an affected part 20 by a beam guide unit 120.

This beam guide unit 120 includes an optical cable 121 for guiding near-infrared ray passing through near-infrared filter 113 to the side of objective lens 130, and a guide reflection mirror 122 for guiding near-infrared ray to reach the objective lens 130 precisely by reflecting near-infrared ray that is transmitted from optical cable 121.

When near-infrared ray guided by the beam guide unit 120 irradiates an affected part 20 through the objective lens 130, the near-infrared ray is reflected by the affected part 20 to form a near-infrared image, and then it is again magnified through the objective lens 130 to reach an image transmission unit 140.

Figure 5:
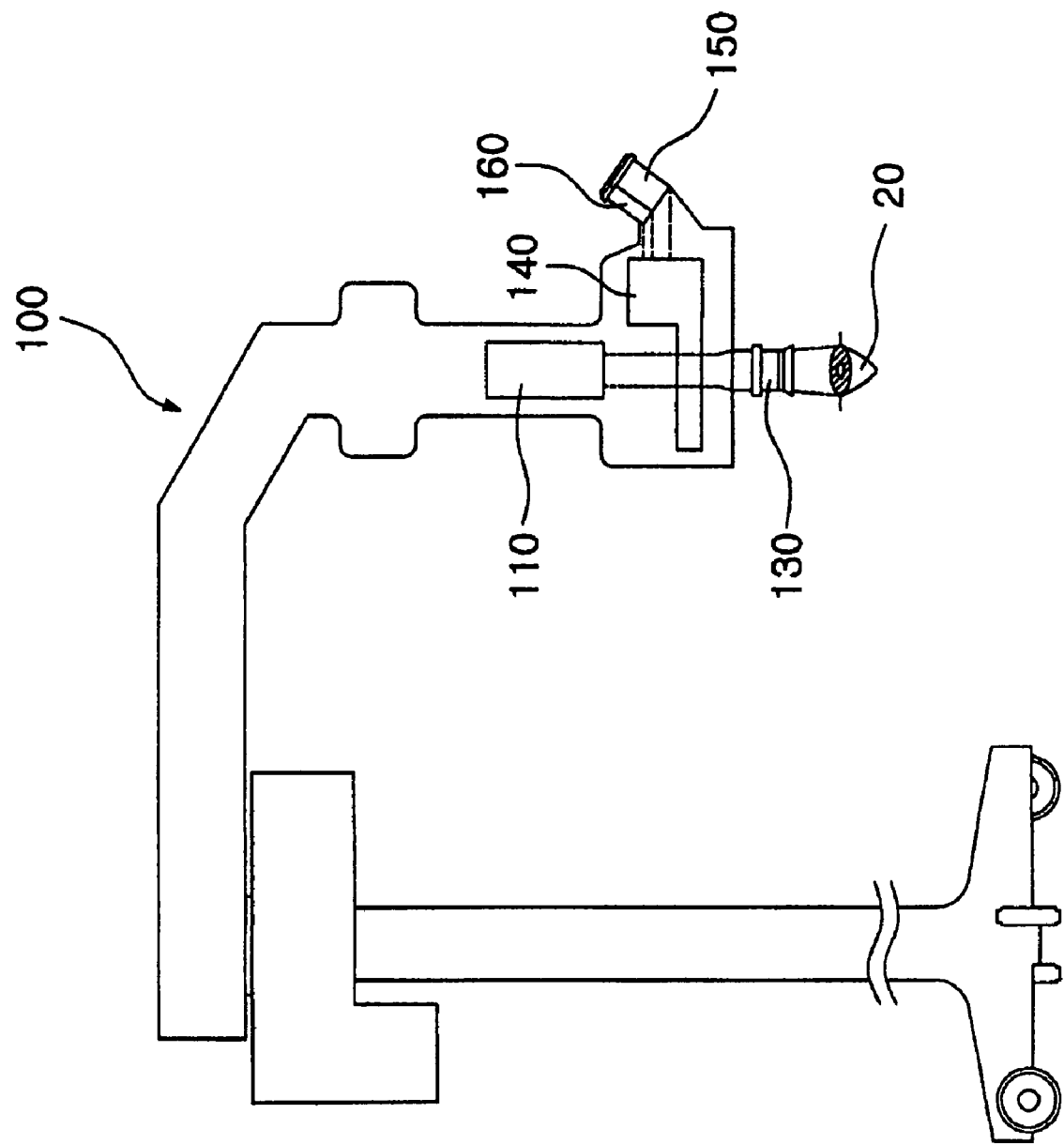
FIG. 5 shows a near-infrared microscope that is arranged to irradiate near-infrared directly through an objective lens by the light source illumination unit shown in FIG. 2.

Of course, at this time, it may be configured so as to irradiate near-infrared ray produced from beam generation unit 110 directly to an affected part 20 through the objective lens 130 without passing through the beam guide unit 120 as shown in FIG. 5.

Moreover, the image transmission unit 140 has two optical paths for transmitting a near-infrared image to ocular lenses 150, 160, and also there are provided an objective lens and at least one reflection mirror in each optical path. Such specific configuration and operation for the image transmission unit 140 is publicly known to skilled persons in the industry involved (e.g., an image transmission unit having two optical paths is disclosed in Japanese Patent Publications No. 1999-155153, and No. 1994-9571, etc.), and the detailed description thereof will be omitted in this specification.

However, near-infrared images that reached ocular lenses 150, 160 through image transmission unit 140 are out of visible light range that is recognizable by the human eyes so that the user cannot observe the images directly through ocular lenses 150, 160.

Thus, the image acquisition apparatus 200 as shown in FIG. 2 performs a function for receiving and sensing a near-infrared image of the affected part 20 that has reached ocular lenses 150, 160, and then converting it into an electrical image signal for output.

Figure 6:
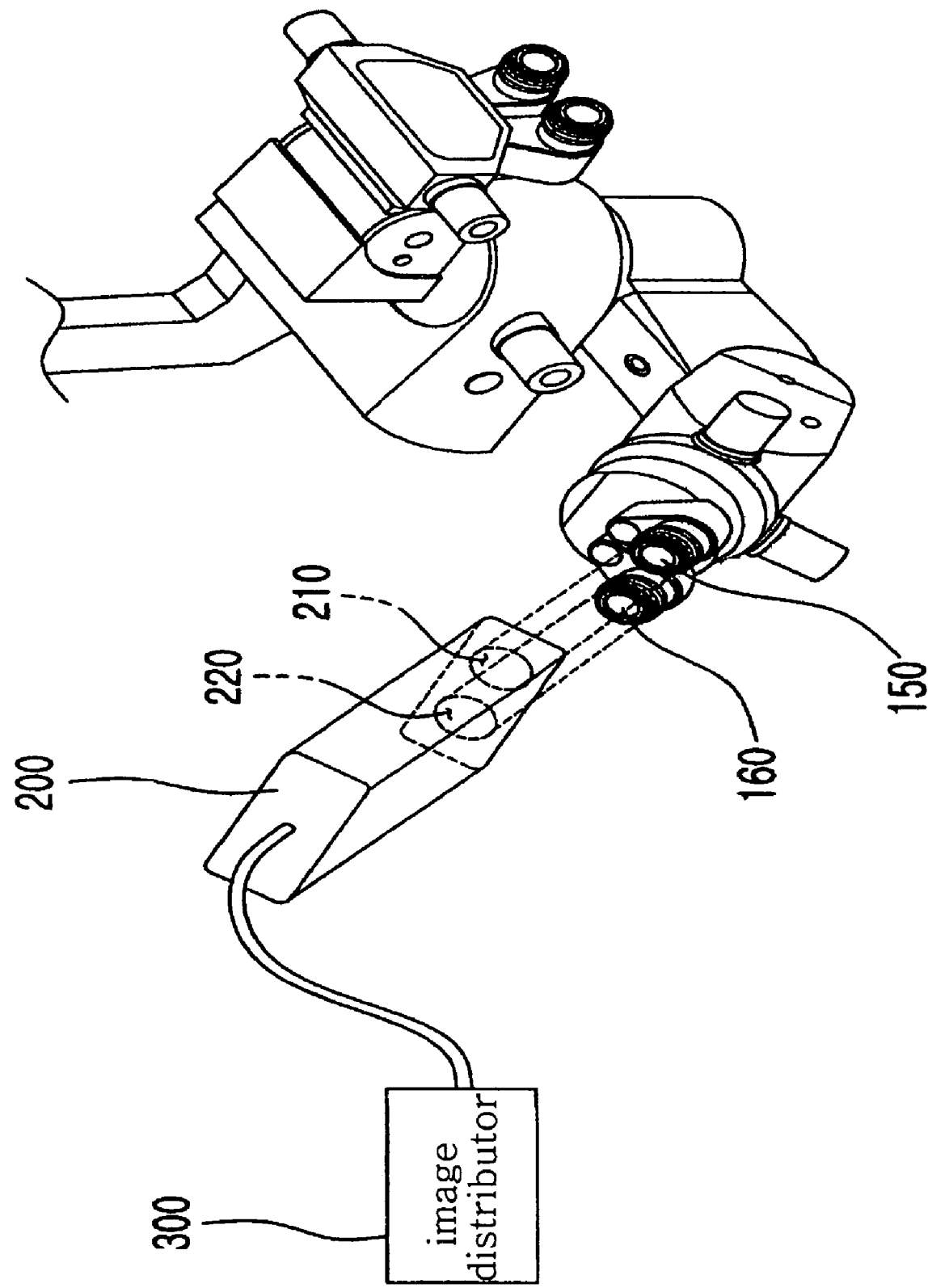
FIG. 6 is a perspective view showing an external shape of an image acquisition apparatus as shown in FIG. 2.
Figure 7:
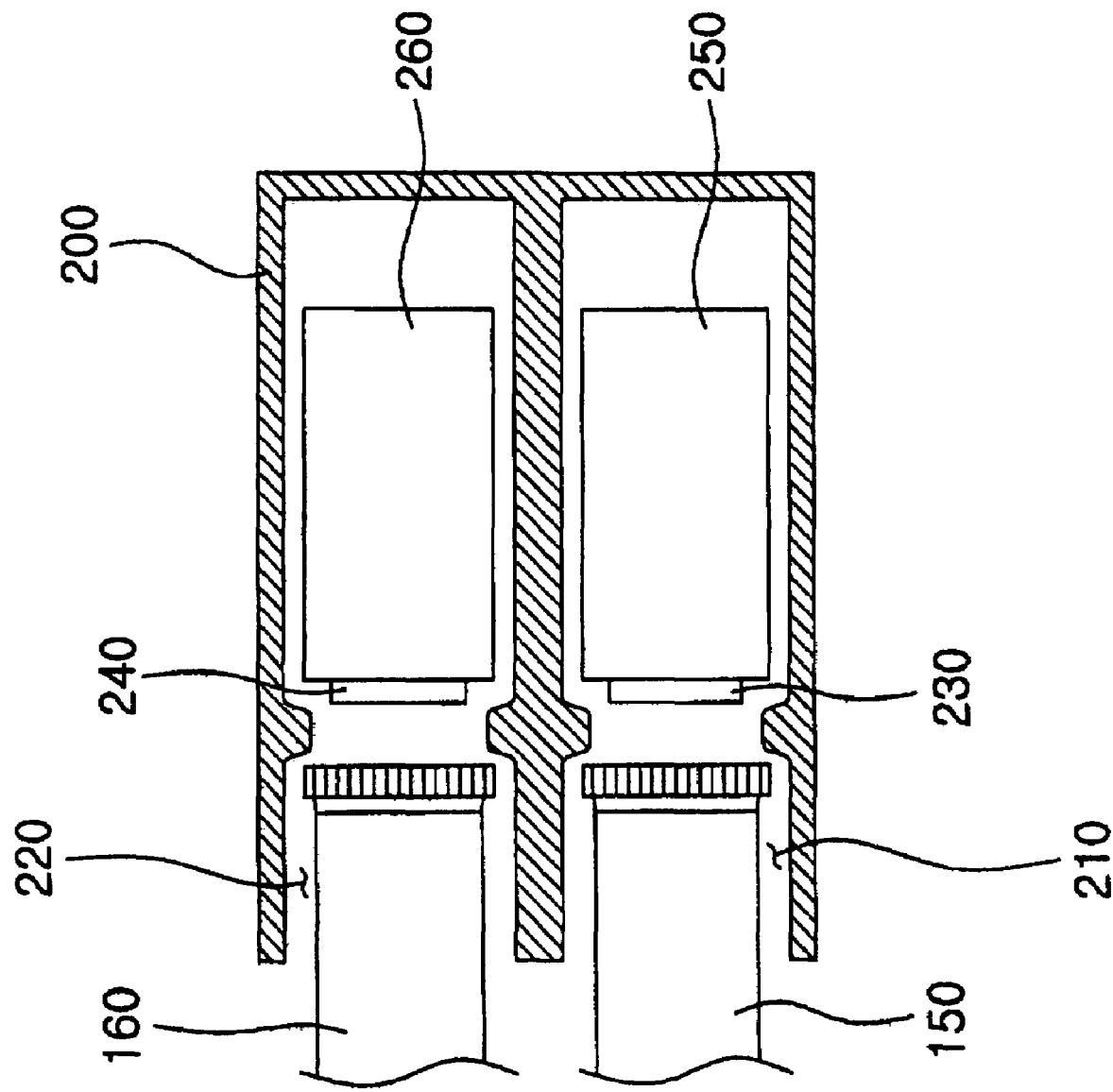
FIG. 7 shows a shape of ocular lenses when they are inserted into the image acquisition apparatus shown in FIG. 5 and an interior configuration of the image acquisition apparatus.

FIG. 6 is a perspective view showing an external shape of the image acquisition apparatus 200 according to one embodiment of the present invention and FIG. 7 is a view schematically showing a shape of the ocular lenses 150, 160 when they are inserted into the image acquisition apparatus 200 of FIG. 6 and an interior configuration of the image acquisition apparatus 200.

In the image acquisition apparatus 200, as shown in FIG. 6, a left side ocular lens insertion groove 210 and a right side ocular lens insertion groove 220 are formed at one side of the body for inserting a left side ocular lens 150 and a right side ocular lens 160.

Furthermore, a left side near-infrared sensor 250 and a right side near-infrared sensor 260 are provided in the left side ocular lens insertion groove 210 and the right side ocular lens insertion groove 220 within the image acquisition apparatus 200 as shown in FIG. 7. Preferably, the left and the right side near-infrared sensors 250, 260 are high-performance CCD sensors respectively, which are capable of sensing not only near-infrared ray but also dark natural light.

Additionally, a left side relay lens 230 and a right side relay lens 240 for transmitting near-infrared images on the left side ocular lens 150 and the right side ocular lens 160 to the left side near-infrared sensor 250 and the right side near-infrared sensor 260, are provided respectively between the left side ocular lens insertion groove 210 and the left side near-infrared sensor 250, as well as between the right side ocular lens insertion groove 220 and the right side near-infrared sensor 260.

Therefore, when the left side ocular lens 150 and the right side ocular lens 160 of the near infrared microscope 100 are simply inserted into the left side ocular lens insertion groove 210 and the right side ocular lens insertion groove 220 of the image acquisition apparatus 200 by the user, near-infrared images on the left side ocular lens 150 and the right side ocular lens 160 are transmitted to the left side near-infrared sensor 250 and the right side near-infrared sensor 260 by the left side relay lens 230 and the right side relay lens 240, so that the left side near-infrared sensor 250 and right side near-infrared sensor 260 can sense the transmitted near-infrared images respectively and convert them into electrical image signals to transmit to an image distributor 300.

At this time, when the user wants to observe an affected part 20 directly through ocular lenses 150, 160 by selecting the visible light pass filter 115 using the filter selection unit 114, it is possible to do so by dismantling the image acquisition apparatus 200 that is combined with ocular lenses 150, 160.

Moreover, the image distributor 300 performs a function for distributing left side image data and right side image data received from an image acquisition apparatus 200 to transmit them to a display apparatus 400 and a control/storage apparatus 500.

The reason for dividing two channel images into a left side image and a right side image is to enable each display apparatus 400 to perform stereo type three-dimensional image display using a visual phase difference between the left side image and the right side image.

The display apparatus 400 performs a function to display three-dimensional images by means of the left and the right side image data that are transmitted from the image distributor, and preferably it may be realized by multiple HMDs 410, which the user can put on the head, or a three-dimensional monitor 420.

Figure 8:
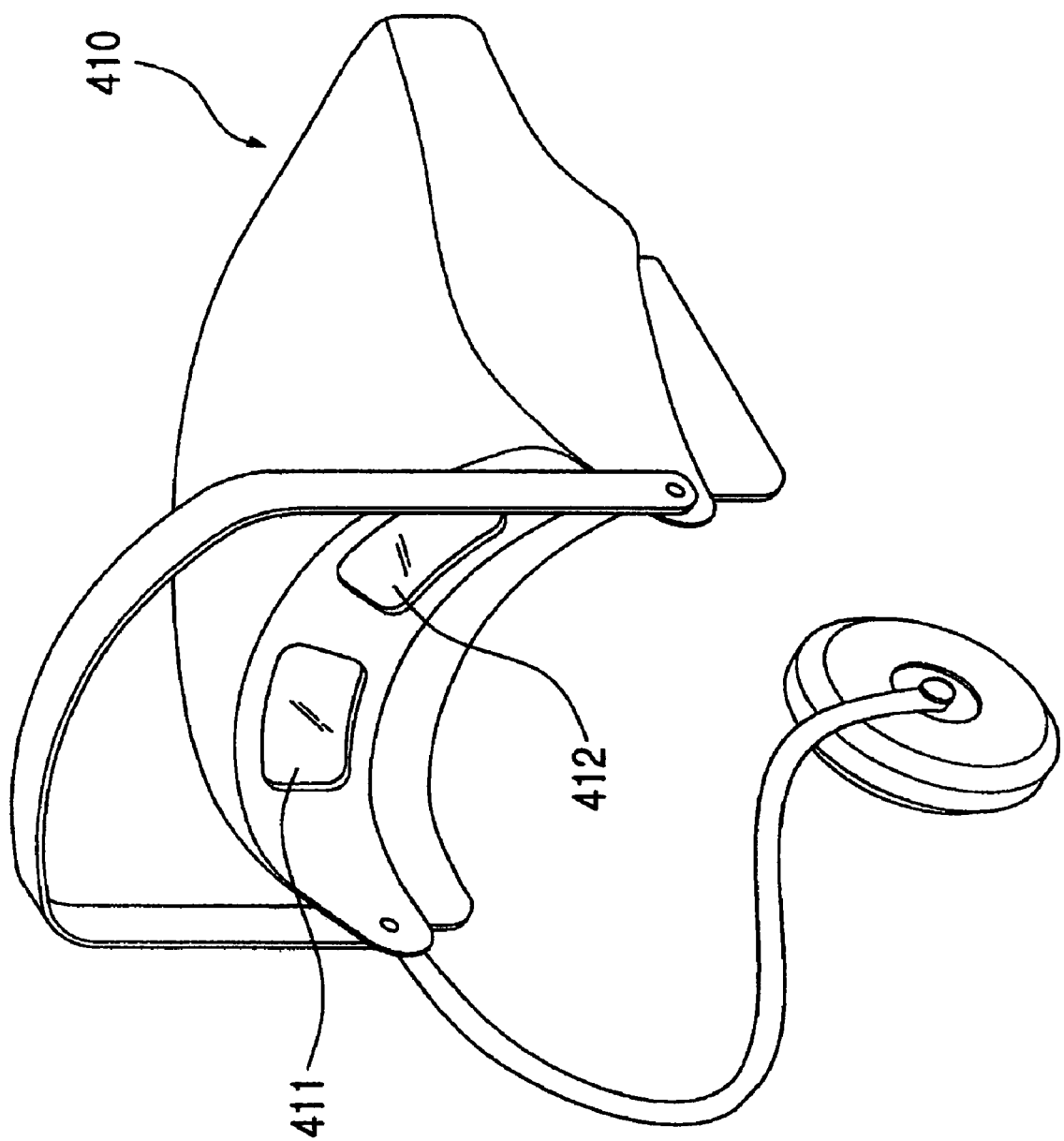
FIG. 8 is a perspective view showing a shape of HMD (Head Mounted Display) as shown in FIG. 2.

As shown in FIG. 8, the HMD 410 is configured with a terminal case so as to be put on the head by the user, and it is provided with a left side screen 411 and a right side screen 412 on the attachment surface, in order to display three-dimensional images through a phase difference between the left side image and the right side image by displaying the left side image data and the right side image data transmitted from the image distributor 300 on the left side screen 411 and the right side screen 412 respectively.

Accordingly, the user can observe three-dimensional images of the affected part 20 by wearing the HMD 410, and when an operation is performed by a plurality of users (operating doctor and his assistants) each user can observe the affected part 20 respectively by wearing multiple HMDs 410 provided.

Furthermore, a plurality of users can perform an operation while observing three-dimensional monitor 420 that is recently developed.

Moreover, various kinds of display environments for the display apparatus 400 are set up by a control/storage apparatus 500 as shown in FIG. 2, and it performs a function for storing the images of affected part 20 that are displayed through the display apparatus 400. At this time, the stored images of an affected part 20 are transformed to a database so that the user can retrieve and reproduce the data when needed.

Furthermore, the images of affected part 20 transmitted through image distributor 300 can of course be stored and reproduced using various kinds of terminals (not shown) such as separate videos or the like.

Moreover, the picture system for ophthalmic operation according to the first embodiment includes a near infrared microscope 100, an image acquisition apparatus 200, an image distributor 300, a display apparatus 400, and a control/storage apparatus 500, but since typical operation microscope is a highly expensive equipment it is possible to provide more inexpensive and economical system by removing the near-infrared microscope 100 from the construction of the first embodiment as stated above.

Figure 9:
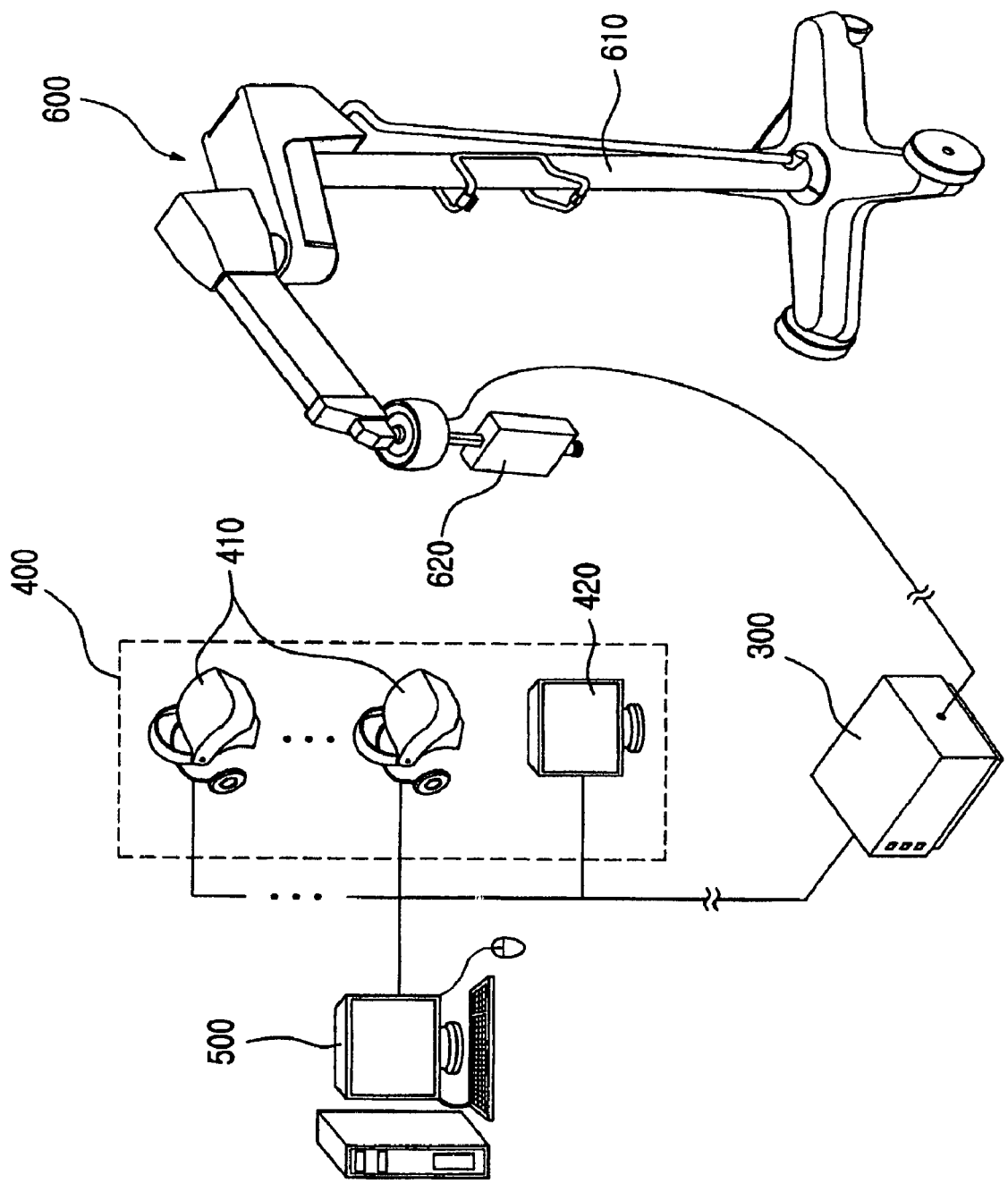
FIG. 9 shows a picture system for ophthalmic operation according to a second embodiment of the present invention.

FIG. 9 is a configuration view showing a picture system for ophthalmic operation according to a second embodiment of the present invention.

As shown in FIG. 9, the picture system for ophthalmic operation according to the second embodiment of the present invention includes an image acquisition/output apparatus 600, an image distributor 300, a display apparatus 400, and a control/storage apparatus 500.

The image acquisition/output apparatus 600 includes a main body 620, and a supporting member 610 which is combined with one side of the main body 620 for supporting the main body 620 to approach an affected part. In addition, the image acquisition/output apparatus 600 performs a function for acquiring near-infrared images of affected part using near-infrared ray, and converting the near-infrared images into electrical image signals to send them to an image distributor 300.

Figure 10:
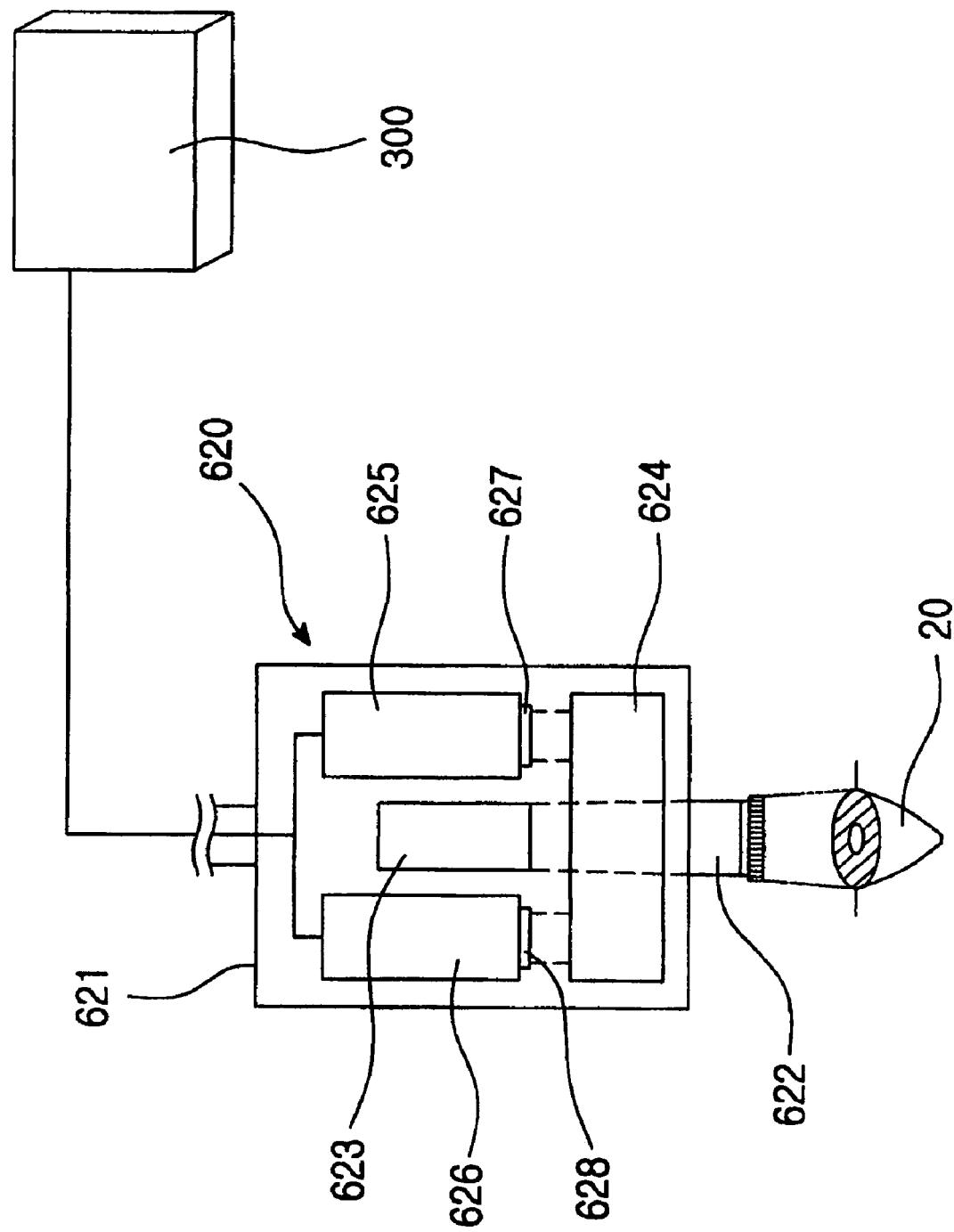
FIG. 10 shows an image acquisition/output apparatus shown in FIG. 9 more specifically.

FIG. 10 is a configuration view schematically showing the main body 620 configuration of the image acquisition/output apparatus 600 as shown in FIG. 9.

As shown in FIG. 10, the main body 620 includes a case 621 having an image acquisition lens 622 at one side, a beam generation unit 623 provided within the case 621, an image transmission unit 624, a left side image acquisition unit 625, and a right side image acquisition unit 626.

At this time, the beam generation unit 623 performs a function for producing near-infrared ray to irradiate an affected part 20 through the image acquisition lens 622. The beam generation unit 623 is configured with a light source 111 and a near-infrared filter 113, as the beam generation unit 110 in the near infrared microscope 100 according to the first embodiment, or it is configured with a near-infrared LED (not shown).

The image transmission unit 624 made of multiple reflection mirrors transmits near-infrared images of affected part that are acquired through the image acquisition lens 622 to the left side image acquisition unit 625 and the right side image acquisition unit 626 respectively.

The left side image acquisition unit 625 and the right side image acquisition unit 626 sense left near-infrared images and right near-infrared images respectively, and convert them into electrical image signals to output to the image distributor 300.

At this time, a left side relay lens 627 and a right side relay lens 628 are provided between the image transmission unit 624 and the left side image acquisition unit 625 or the right side image acquisition unit 626 in order to transmit the left near-infrared images and the right near-infrared images respectively to the left side image acquisition unit 625 and the right side image acquisition unit 626.

On the other hand, the function and operation of the image distributor 300, the multiple display apparatuses 400 and the control/storage apparatus 500 are identical to those of the foregoing embodiment. In other words, the image distributor 300 distributes and transmits left side image data and right side image data received from the image acquisition/output apparatus 600 to each display apparatus 400, and the display apparatus 400 displays three-dimensional images through receiving the left side image and the right side image data.

Accordingly, three-dimensional images can be displayed on multiple display apparatuses 400 after acquiring an image of affected part 20 using the image acquisition/output apparatus 600 without having a near-infrared microscope 100.

Moreover, it is possible to work a system (a third embodiment) in which a near-infrared microscope is utilized as disclosed in the first embodiment, and further a beam splitter capable of dividing an image is provided with the near infrared microscope, thereby acquiring the images divided by the beam splitter.

Hereinafter, a picture system for ophthalmic operation according to the third embodiment of the present invention will be described with reference to FIG. 11 through FIG. 13.

Figure 11:
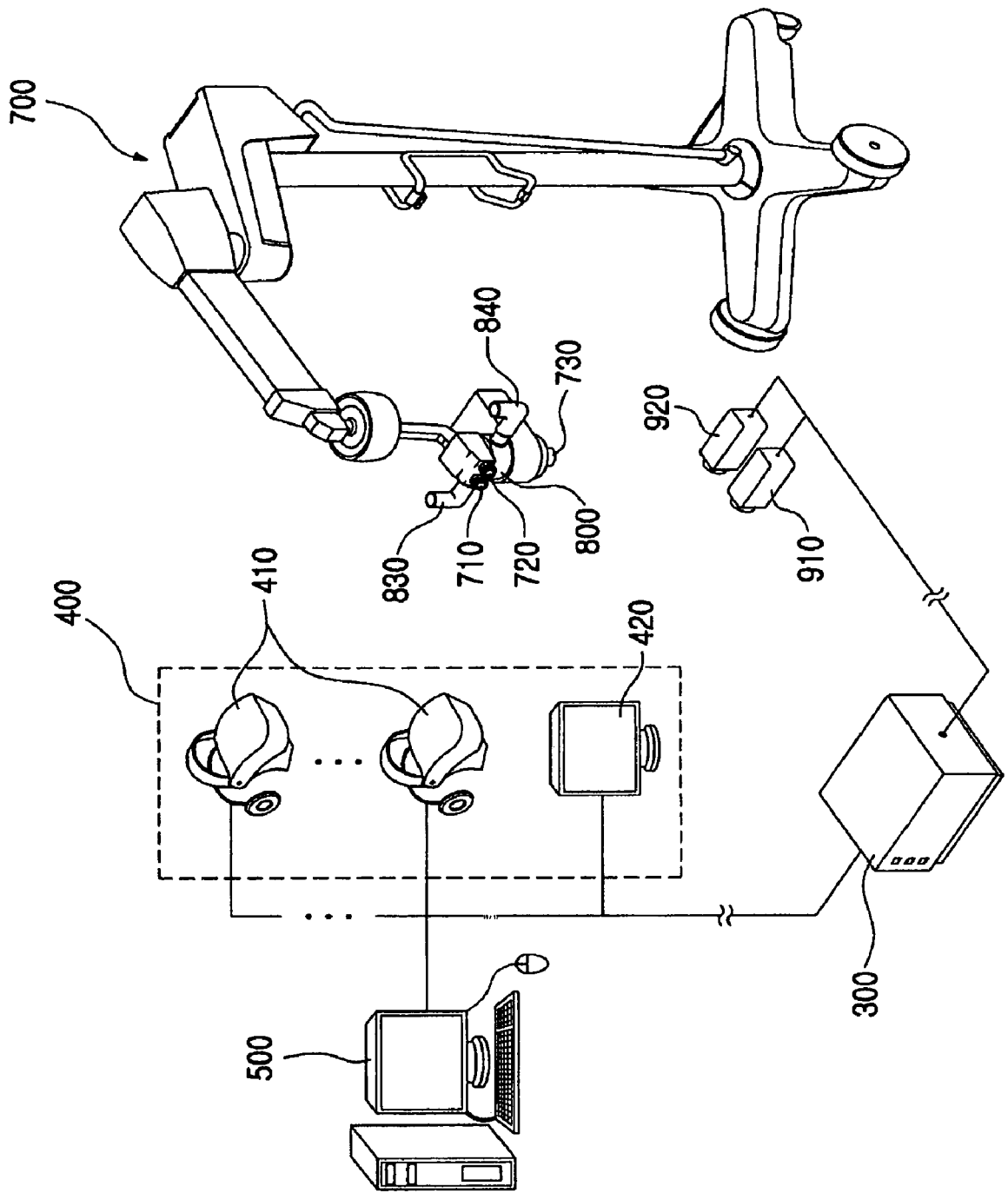
FIG. 11 is a perspective view showing an ophthalmic operation near-infrared microscope according to a third embodiment of the present invention.
Figure 12:
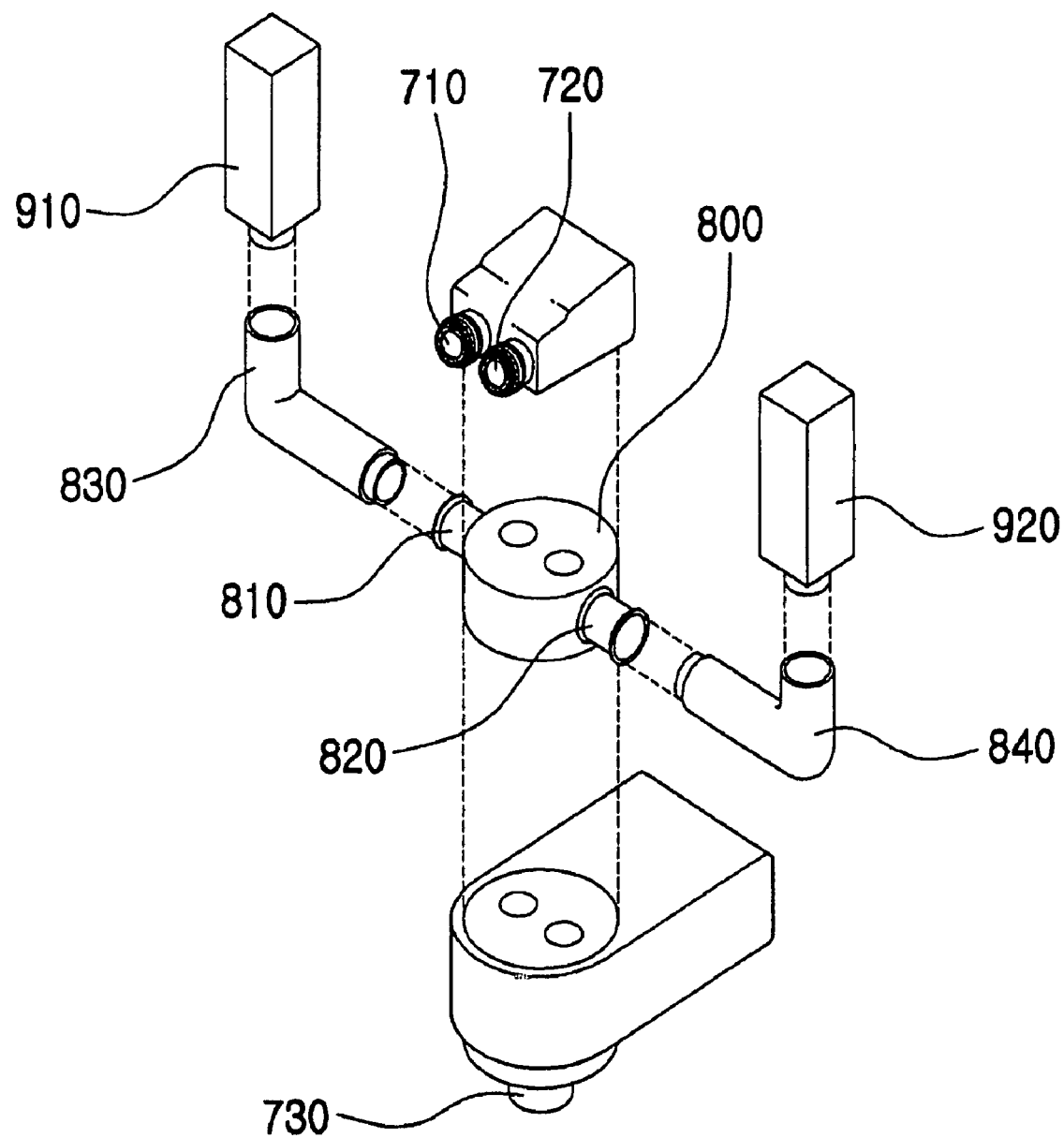
FIG. 12 is an exploded perspective view showing a configuration in which a near-infrared microscope is combined with a beam splitter and left/right side image acquisition apparatuses as shown in FIG. 11.
Figure 13:
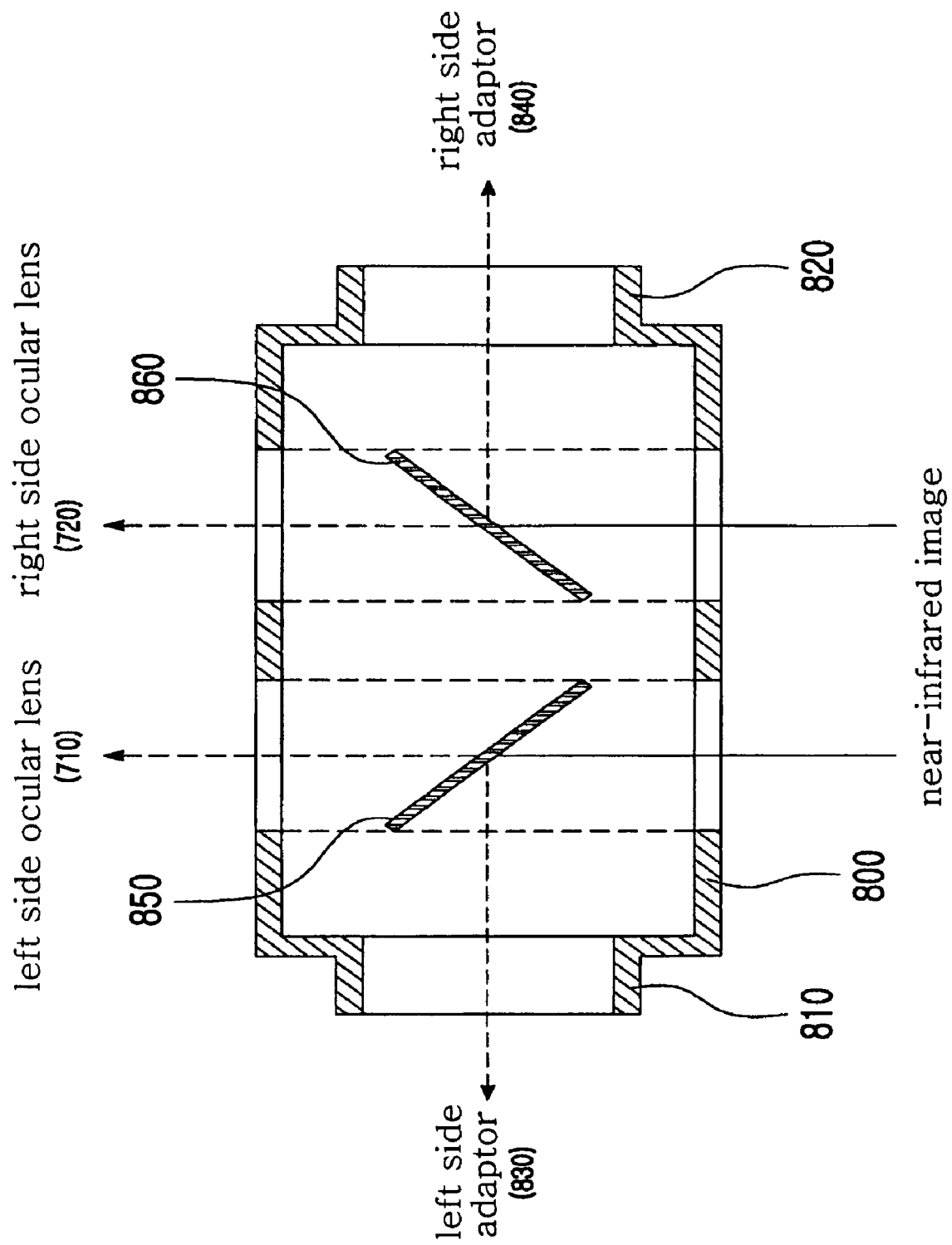
FIG. 13 is a cross sectional view showing a structure of the beam splitter as shown in FIG. 12.

FIG. 11 is a perspective view showing a configuration of the ophthalmic operation near-infrared microscope according to the third embodiment of the present invention, and FIG. 12 is an exploded perspective view showing a configuration in which a near-infrared microscope 700 is combined with a beam splitter 800 and left/right side image acquisition apparatuses 910, 920 as shown in FIG. 11. Furthermore, FIG. 13 is a cross sectional view showing a construction of the beam splitter 800 of FIG. 12.

As shown in FIG. 11, the picture system for ophthalmic operation according to the third embodiment includes a near-infrared microscope 700, a beam splitter 800, a left side adaptor 830, a right side adaptor 840, a left side image acquisition apparatus 910, a right side image acquisition apparatus 920, an image distributor 300, a display apparatus 400, and a control/storage apparatus 500. Here, the display apparatus 400 and the control/storage apparatus 500 are identical to those of the first and the second embodiments, and the detailed description thereof will be omitted here.

The near-infrared microscope 700 includes a power source 170, a beam generation unit 110, and a beam guide unit 120 as disclosed in the first embodiment. As shown in FIG. 12, however, the beam splitter 800 is inserted between an objective lens 730 and ocular lenses 710, 720, instead of an image transmission unit 140 as disclosed in the first embodiment.

At this time, combining ends 810, 820 for combining a left side adaptor 830 and a right side adaptor 840 with them respectively are formed at both sides of the beam splitter 800. Within the beam splitter, furthermore, it is provided with a left side image dividing unit 850 and a right side image dividing unit 860 for dividing near-infrared images received from the objective lens 730 and sending them to the left/right side ocular lenses 710, 720 as well as the left side adaptor 830 and the right side adaptor 840, which are combined at the both sides.

Furthermore, a left side image acquisition apparatus 910 and a right side image acquisition apparatus 920 are combined with the ends of the left side adaptor 830 and the right side adaptor 840 to sense the images received from the left side image dividing unit 850 and the right side image dividing unit 860.

Therefore, an affected part can be observed directly through the left side ocular lens 710 and the right side ocular lens 720, or the images acquired by the left side image acquisition apparatus 910 and the right side image acquisition apparatus 920 can be observed by the user in three-dimensional images.

The picture system for ophthalmic operation according to one embodiment of the present invention has been described as stated above. While the present invention has been described with reference to the particular illustrative embodiments, it will be understood by those skilled in the art that the scope of the present invention is not limited to these embodiments but various modifications may be made without departing from the essence of the present invention.

INDUSTRIAL APPLICABILITY

The present invention can be utilized for medical equipment industry, in particular, for the industry related to picture system for ophthalmic operations.

What is claimed is:

1. A picture system for ophthalmic operation comprising:
a near-infrared microscope for irradiating near-infrared rays emitted from a light source to an affected through an objective lens, and transmitting near-infrared images formed by the objective lens to first and second ocular lenses;
an image acquisition apparatus for converting the near-infrared images transmitted to the first and the second ocular lenses into first and second electrical image signals for output, wherein the image acquisition apparatus is detachably combined with the first and the second ocular lenses;
a display apparatus for receiving the first and the second image signals, and outputting the first and second image signals in three-dimensions, the display apparatus including a plurality of display units, wherein each of the display units receives and outputs the first and second electrical image signals; and
an image distributor for distributing and transmitting the first and the second electrical image signals from the image acquisition apparatus to the display units.

2. The picture system for ophthalmic operation according to claim 1, wherein the near-infrared microscope farther comprises an image transmission unit for transmitting near-infrared images that are reflected by the affected part to the first and the second ocular lenses respectively through optical paths different from each other.

3. The picture system for ophthalmic operation according to claim 2, wherein the near-infrared microscope further comprises a near-infrared filter for passing only signals having wavelength in near-infrared region among the rays emitted from the light source.

4. The picture system for ophthalmic operation according to claim 3, wherein a visible light reflection filter for reflecting visible light is jointed at the front surface of the near-infrared filter.

5. The picture system for ophthalmic operation according to claim 3, wherein the near-infrared filter is provided in a filter selecting unit, and a plurality of transmission filters for each wavelength, including the near-infrared filter and the visible light filter, are provided in the filter selecting unit.

6. The picture system for ophthalmic operation according to claim 2, wherein the near-infrared microscope further comprises an optical cable for transmitting near-infrared rays output from the light source, and a guide reflecting mirror for guiding the near-infrared rays transmitted by the optical cable to the objective lens.

7. The picture system for ophthalmic operation according to claim 1, wherein the light source comprises a near-infrared LED, and the affected part is irradiated by near-infrared rays output from the near-infrared LED.

8. The picture system for ophthalmic operation according to claim 1, wherein the image acquisition apparatus comprises:
a body formed with a first and a second inserting grooves in which the first and the second ocular lenses are inserted and fixed;
sensors for sensing near-infrared images output from the first and the second ocular lenses and converting them into the first and the second image signals; and
relay lenses for transmitting near-infrared images output from the first and the second ocular lenses to the sensors.

9. The picture system for ophthalmic operation according to claim 8, wherein the sensors are charge-coupled devices (CCD).

10. The picture system for ophthalmic operation according to claim 1, wherein the display apparatus is a HMD (Head Mounted Display) or a three-dimensional monitor.

11. The picture system for ophthalmic operation according to claim 1, further including a control/storage apparatus for setting and controlling display environments of the display apparatus, and storing images displayed by the display apparatus.

12. The picture system for ophthalmic operation according to claim 11, wherein the control/storage apparatus creates database for retrieval and reproduction of the stored images.

13. An image acquisition/output apparatus including a main body and a supporting member for supporting the main body, the main body including:
an objective lens arranged opposite to an affected part;
a beam irradiation unit for irradiating the affected part with a beam having a predetermined wavelength bandwidth, wherein the beam irradiation unit includes at least two filters having different light sources and transmission bandwidths;
an image acquisition unit for converting images formed by the objective lens into electrical image signals and outputting the electrical image signals;

an image transmission unit for transmitting the images formed by the objective lens to the image acquisition unit; and an image distributor for distributing and transmitting the electrical image signals to a plurality of display units for displaying the electrical image signals in three-dimensions.

14. The image acquisition/output apparatus according to claim 13, wherein the main body further includes relay lenses for connecting the image transmission unit to the image acquisition unit.

15. The image acquisition/output apparatus according to claim 13, wherein the beam irradiation unit includes a near-infrared filter for transmitting the wavelengths corresponding to near-infrared region only.

16. The image acquisition output apparatus according to claim 15, wherein a visible light reflection filter for reflecting visible light is jointed at the front surface of the near-infrared filter.

17. A picture system for ophthalmic operation comprising:
an objective lens arranged opposite to an affected part;
a beam irradiation unit for irradiating the affected part with a beam having a predetermined wavelength bandwidth, wherein the beam irradiation unit includes at least two filters having different light sources and transmission bandwidths;
an image acquisition unit for converting images formed by the objective lens into electrical image signals and outputting the electrical image signals;
an image transmission unit for transmitting the images formed by the objective lens to the image acquisition unit;
an image distributor for distributing and transmitting the electrical image signals to a plurality of display units for displaying the electrical image signals in three-dimensions; and
a display apparatus for outputting three-dimensional images using the electrical image signals outputted from the image acquisition unit.

18. A picture system for ophthalmic operation comprising:
a near-infrared microscope for irradiating near-infrared ray to an affected part by guiding it to an objective lens, and transmitting near-infrared images formed by the objective lens to left and right ocular lenses;
a beam splitter arranged between the objective lens and the left and the right ocular lenses for dividing the near-infrared images into left side and right side near-infrared images and for transmitting the left side and the right side near-infrared images;
a first adaptor connected to one end of the beam splitter for receiving and outputting the left side near-infrared images;
a second adaptor connected to the other end of the beam splitter for receiving and outputting the right side near-infrared images;
a first image acquisition apparatus for outputting the left side near-infrared images output from the first adaptor as left side electrical image signals;
a second image acquisition apparatus for outputting the right side near-infrared images output from the second adaptor as right side electrical image signals;
a plurality of display apparatuses for receiving the left side and the right side electrical image signals and outputting the left side and right side electrical image signals in three-dimensional images respectively, each of the display apparatuses receiving and outputting the left side and the right side electrical image signals; and
an image distributor for distributing and transmitting the left side electrical image signals and the right side electrical image signals from the first and the second image acquisition apparatuses to each of the display apparatuses.

19. The picture system for ophthalmic operation according to claim 18, further comprising a control/storage apparatus for setting and controlling display environments of the display apparatuses respectively, and storing images being displayed by the display apparatuses.

* * * * *